United States Patent [19]

Davis et al.

[11] 4,368,996
[45] Jan. 18, 1983

[54] PENETRAMETER POSITIONER FOR BORE-SIDE RADIOGRAPHY OF TUBES

[75] Inventors: Earl V. Davis; Billy E. Foster, both of Oak Ridge, Tenn.

[73] Assignee: The United States of America as represented by the United States Department of Energy, Washington, D.C.

[21] Appl. No.: 228,838

[22] Filed: Jan. 27, 1981

Related U.S. Application Data

[63] Continuation of Ser. No. 118,379, Feb. 2, 1980, abandoned.

[51] Int. Cl.$^3$ .............................................. F16D 1/08
[52] U.S. Cl. ....................................... 403/5; 279/2 A; 269/48.1; 403/27
[58] Field of Search .................... 403/5, 27; 279/2 A, 279/2 R; 269/48.1

[56] References Cited

U.S. PATENT DOCUMENTS

2,747,100  5/1956  Wyllie et al. .
3,166,335  1/1965  Mason ...................................... 279/2
3,220,840  11/1965  Yackel et al. .
3,535,518  10/1970  Fischer .
3,910,098  10/1975  Tailhardat ...................... 269/48.1 X

FOREIGN PATENT DOCUMENTS

1109466  of 1961  Fed. Rep. of Germany ..... 269/48.1

Primary Examiner—Andrew V. Kundrat
Attorney, Agent, or Firm—Louis M. Deckelmann; Stephen D. Hamel; Richard G. Besha

[57] ABSTRACT

A positioner is provided for placing plaque or wire penetrameters, as used in radiographic inspection, in close proximity with the inner wall of tubing at any desired location along the tubing. The positioner head carrying the penetrameter is inflatable whereby it is positioned in the deflated condition, inflated to place the penetrameter against a weld to be inspected in the tubing wall, and then deflated during removal. If desired, the penetrameter holder may be used to center the radiographic source on the axis of the tube.

6 Claims, 3 Drawing Figures

PENETRAMETER POSITIONER FOR BORE-SIDE RADIOGRAPHY OF TUBES

This is a continuation of application Ser. No. 118,379, filed Feb. 2, 1980 and now abandoned.

BACKGROUND OF THE INVENTION

The present invention relates to a penetrameter positioner for bore-side radiography of tubes and more particularly to an improved positioner for providing easy insertion or removal of the positioner to or from the desired point of inspection and including means for placing the penetrameter against the tubing wall at the point of inspection. It is the result of a contract with the U.S. Department of Energy.

An image-quality indicator (IQI), otherwise known as a penetrameter, is needed in radiographic examination to assure a consistent image. American industry commonly uses a plaque consisting of a thin shim with right-cylindrical holes. Both the thickness of the shim and the diameter of the holes are fractional parts of the specimen thickness (such as 2%). However, there are usually minimum dimensions on the penetrameter which reduce its validity and usefulness for thin materials, typically less than about 6.0 mm (¼ inch). A further complicating factor for radiography of tube-to-tubesheet joints with a coaxial radiation source is that adequate film densities are normally achieved only in the immediate vicinity of the weld. For its image to show, the penetrameter would need to be placed on the weld. However, such placement would confuse the interpretation because the image of the penetrameter holes would be superimposed on the image of the weld.

Another type of penetrameter is also used, particularly in Europe. This penetrameter contains small-diameter wires and can be superimposed on a weld without confusing the interpretation.

For radiography the penetrameters are placed source-side of the weld, if possible. In bore-side inspection of tubing welds, the placement of the penetrameters is on the outer surface of the target holder for x-radiography and on the outer surface of the source tube for isotope radiography. Film for recording the penetrating radiation is placed exterior to the tube weld using a cassette such as that described in U.S. Pat. No. 3,952,204, to Earl V. Davis et al, issued Apr. 20, 1976. Since the weld may be located several meters from an end of the tubing, sufficient clearance must be permitted about the penetrameter holder to permit easy insertion or removal of the radiation source. Different values of clearance may be experienced when tubing diameter varies. This clearance, however, prevents placing the penetrameter in close proximity to the weld and thus reduces resolution of the penetrameter image.

It is, therefore, an object of the present invention to provide a device for easily positioning a penetrameter (and source of radiation) into and from long tubing and yet permit placing the penetrameter in close proximity to the weld surface to be radiographed.

Other objects, advantages and novel features of the invention will become apparent to those skilled in the art upon examination of the following detailed description of a preferred embodiment of the invention and the accompanying drawings.

SUMMARY OF THE INVENTION

A positioner holder is provided for placing a plaque or wire penetrameter, as used in radiographic inspection, in close proximity with the inner wall of tubing at any desired inspection location along the tubing. The holder surrounds a source of radiation for bore-side radiography of tubing welds. The holder is provided with means for minimizing radial dimensions during insertion and removal of the source and holder relative to the tubing, and with means for moving the penetrameter or plaque radially into close proximity of the weld surface prior to the radiographic inspection of the weld. In the preferred form, the radial movement of the penetrameter or plaque is accomplished by inflating (and subsequent deflating) an expandable cylindrical member.

DESCRIPTION OF THE PREFERRED EMBODIMENT

Figure 1:
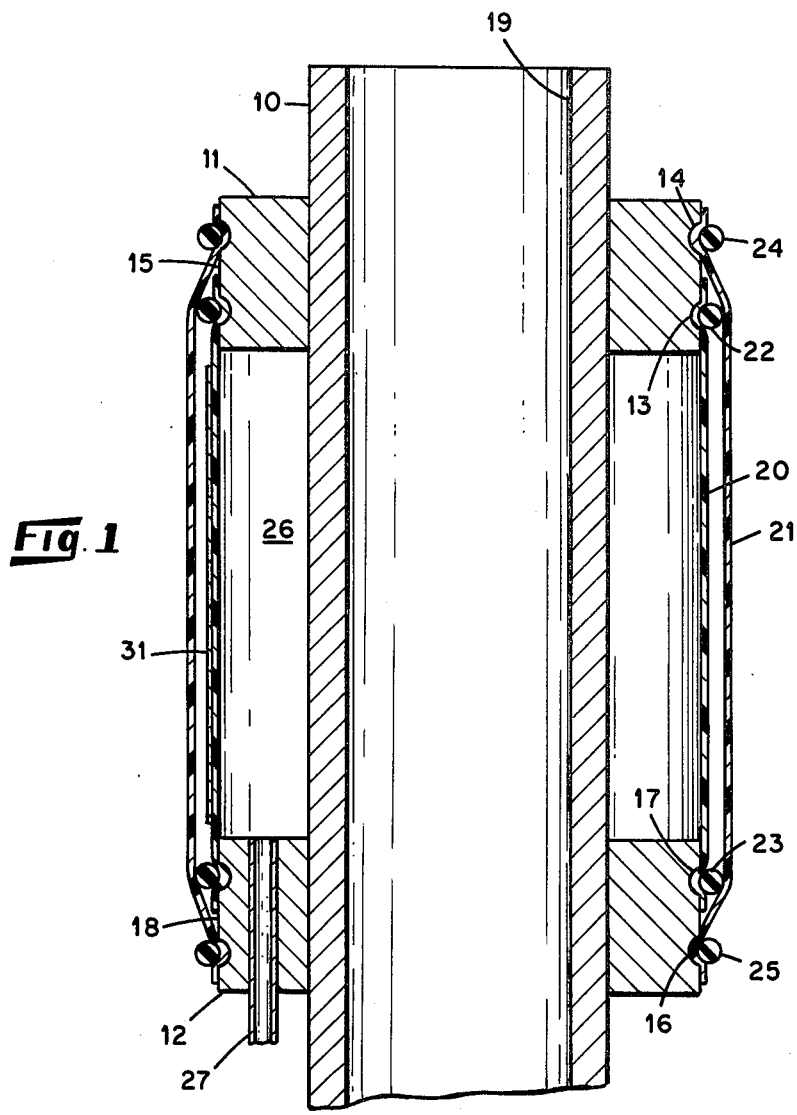
FIG. 1 is a cross-sectional view of one embodiment of a penetrameter holder designed to permit easy insertion and removal from a tube, but yet permitting placement of the penetrameter against a tubing weld during radiographic inspection.

Referring now to FIG. 1, the body of the penetrameter holder is a spool piece made up of a tube 10 and two support rings 11, 12 attached to the tube in any suitable manner near the end thereof. Support ring 11 is provided with a pair of annular grooves 13, 14 in its outer surface 15, and support ring 12 has similar grooves 16, 17 in its outer surface 18. The tube bore 19 accommodates a source of radiation, not shown, and is adapted to be attached to the radiation source unit.

Surrounding the spool, and releasably attached to support rings 11, 12 is a pair of concentric cylindrical fluid-impermeable membranes or sleeves 20, 21, these sleeves being formed of an elastic material such as rubber. The inner membrane 20 is attached to bobbins 11, 12 using elastomer rings 22, 23 which fit into the grooves 13, 17. The outer sleeve 21 is similarly attached using elastomer rings 24, 25 fitting into grooves 14, 16. A penetrameter is mounted to the outer surface of the sleeve 20 and is thus positioned between the sleeves 20, 21. A plurality of wires 31 are mounted in parallel along the outer surface of the sleeves 20, only one such wire being shown in cross section in FIG. 1 and shown enlarged for the sake of clarity. These wires constitute the penetrameter. Alternately, a plaque or a number of plaques could be utilized in the device of FIG. 1, if desired, and such means would be mounted on the outer surface of the sleeve 20. The above-mentioned radiation source unit is mounted inside the tube 10 at a position in radial alignment with the penetrameter wires 31, mentioned above. Fluid communication is made to the volume 26 between the inner sleeve 20 and the tube 10 by a conduit 27 passing through support ring 12. A source of fluid, not shown, is adapted to be connected to the external end of the conduit 27.

Figure 2A:
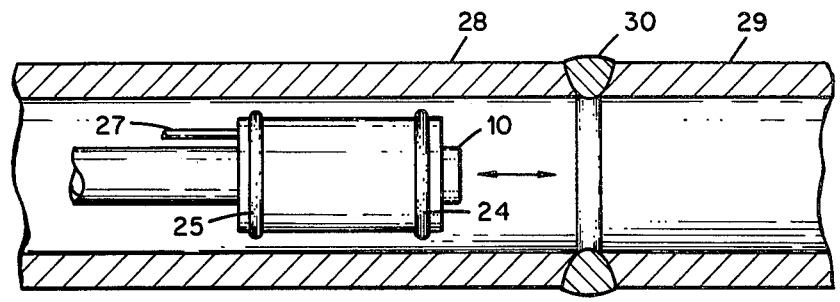
FIG. 2a is a cross-sectional view of the penetrameter holder in an unexpanded condition within a tubing.
Figure 2B:
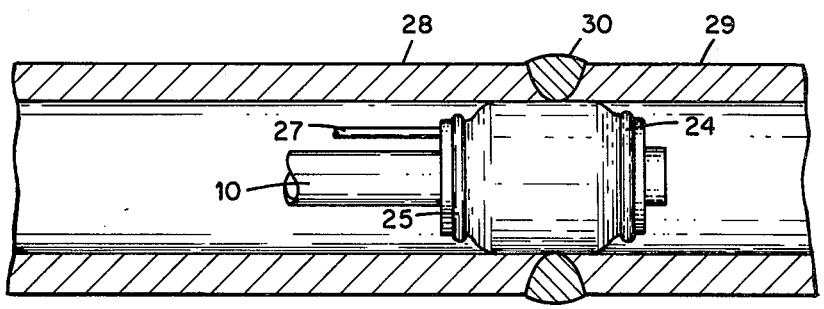
FIG. 2b is a cross-sectional view of the penetrameter in an expanded position within a tubing.

The outer diameter of retaining rings 24, 25 is chosen to be less than the inner diameter of any tubing to be inspected. Thus, the penetrameter holder may be easily inserted into such tubing to the axial position where radiographic examination is desired. This condition is illustrated in FIG. 2a. When properly positioned an appropriate fluid (gas or liquid) is used to pressurize volume 26 by means of the conduit 27 and thereby radially expand sleeves 20, 21, moving the penetrameter(s) positioned therebetween outwardly into close proximity to the weld 30, joining the tubing 28, 29, to be examined. This is illustrated in FIG. 2b. Release of the pressure in volume 26 permits radial contraction of the sleeves 20, 21 to permit easy removal of the holder after the radiography of the weld 30 has been effected. It should be understood that the lengths of the tube 10 and the fluid feed conduit 27 are made sufficiently long to permit the insertion of the holder into a tubing to be inspected to the position of a weld joint to be radiographed.

The foregoing description of a preferred embodiment of the invention has been presented for purposes of illustration and description and is not intended to be exhaustive or to limit the invention to the precise form disclosed. It was chosen and described in order to best explain the principles of the invention and their practical application to thereby enable others skilled in the art to best utilize the invention in various embodiments as are suited to the particular use contemplated. For example, the membranes could be permanently attached about the bobbins rather than using elastomer rings. In another version, the holder itself is provided with expandable segments. In still another version, such expandable segments may be adapted to be moved radially using mechanical elements which may be manipulated with fluid pressure or mechanical connections. It is intended that the scope of the invention be defined by the claims appended hereto.

What is claimed is:

1. Apparatus for positioning an object adjacent a wall comprising:
   a tube;
   a pair of elastic sleeves concentrically disposed around said tube adjacent one end thereof, the ends of said sleeves being secured to said tube and said sleeves intermediate their ends being expandable outwardly from said tube, said object which is to be positioned adjacent said wall being disposed between said sleeves; and
   means for expanding said sleeves outwardly from said tube to move said object adjacent said wall.

2. Apparatus for positioning an object adjacent the inner wall of a pipe or the like, comprising:
   a tube;
   a pair of support rings disposed around said tube adjacent one end thereof, said support rings being spaced apart longitudinally of said tube;
   a pair of elastic sleeves concentrically disposed around said tube, the ends of each of said sleeves being respectively disposed around and secured to said support rings to provide an annular space between said tube and said sleeves, said object which is to be positioned adjacent said inner wall being disposed between said sleeves; and
   means for pressurizing said annular space between said tube and the inner one of said sleeves to expand both of said sleeves outwardly from said tube and move said object to a position adjacent said wall.

3. Apparatus as defined in claim 2 wherein grooves extend circumferentially of each of said support rings, and including retaining rings respectively disposed around said sleeves and cooperating with said grooves to secure said sleeves to said support rings.

4. Apparatus as defined in claim 2 wherein said means for pressurizing said annular space comprises a fluid supply conduit communicating with said annular space through a hole extending through one of said support rings.

5. Apparatus as defined in claim 2 wherein said object to be positioned adjacent said wall is mounted on the inner one of said sleeves.

6. Apparatus as defined in claim 5 wherein said object is a penetrameter.

* * * * *